United States Patent
Hoffman et al.

(10) Patent No.: US 11,051,987 B2
(45) Date of Patent: Jul. 6, 2021

(54) METHOD FOR TAILORING A COMPRESSION GARMENT

(71) Applicant: SIGVARIS AG, St. Gallen (CH)

(72) Inventors: Keith Hoffman, Hudsonville, MI (US); Daniel W. Karadsheh, Zeeland, MI (US); Laure Kuipers, Holland, MI (US)

(73) Assignee: Sigvaris AG, St.Gallen (CH)

( * ) Notice: Subject to any disclaimer, the term of this patent is extended or adjusted under 35 U.S.C. 154(b) by 414 days.

(21) Appl. No.: 16/058,976

(22) Filed: Aug. 8, 2018

(65) Prior Publication Data

US 2018/0344532 A1 Dec. 6, 2018

Related U.S. Application Data

(63) Continuation-in-part of application No. 15/808,092, filed on Nov. 9, 2017, now Pat. No. 10,820,648, and
(Continued)

(51) Int. Cl.
*A61F 13/00* (2006.01)
*A61F 13/06* (2006.01)
*A61F 13/08* (2006.01)

(52) U.S. Cl.
CPC ........ *A61F 13/00059* (2013.01); *A61F 13/06* (2013.01); *A61F 13/085* (2013.01); *A61F 2013/0028* (2013.01)

(58) Field of Classification Search
CPC ............. A61F 13/08; A61F 13/085; A61F 2013/0028; A61F 13/0273;
(Continued)

(56) References Cited

U.S. PATENT DOCUMENTS

| | | | |
|---|---|---|---|
| 2,687,723 A | 8/1954 | Stern | |
| 3,613,679 A | 10/1971 | Bijou | |

(Continued)

FOREIGN PATENT DOCUMENTS

| | | | |
|---|---|---|---|
| AU | 6414174 A | 7/1975 | |
| AU | 2017329457 A1 | 2/2019 | |

(Continued)

OTHER PUBLICATIONS

CircAid JuxtaFit Essentials arm sleeve by Medi; http://mediusa.com/portfolio-item/juxtafit-essentials-upper-extremity/; Mar. 29, 2015.
(Continued)

*Primary Examiner* — Ophelia A Hawthorne
(74) *Attorney, Agent, or Firm* — FisherBroyles LLP; Anthony J DoVale

(57) ABSTRACT

A method and system for tailoring a compression garment having a first lateral end and a second lateral end. A first tension tab releasably attachable to the compression garment; wherein the first tension tab includes at least a first indicator and a second indicator on an outer surface. The first tension tab being attachable to the compression garment and the first strap being attachable onto the compression garment adjacent or over at least a portion of the first tension tab with a first strap covering a first part of the first tension tab and terminating at a first strap end that exposes a second portion of the first tension tab. A first tension tab setting indicates whether the end of the first strap terminates adjacent or over the first indicator or the second indicator of the first tension tab.

18 Claims, 6 Drawing Sheets

Related U.S. Application Data a continuation-in-part of application No. 15/443,308, filed on Feb. 27, 2017, now Pat. No. 10,898,390.

(58) Field of Classification Search
CPC .......... A61F 2013/00119; A61F 13/108; A61F 15/006; A61F 2013/00174; A61F 2013/00468; A61F 13/00008; A61F 13/022; A61F 13/0269; A61F 2013/00565; A61F 2013/00957; A61F 5/37; A61F 2013/00131; A61F 13/062; A61F 15/004; A61F 2013/00093; A61F 13/00029; A61F 13/00034; A61F 13/0226; A61F 13/066; A61F 13/533; A61F 13/55185; A61F 13/62; A61F 2007/0231; A61F 2013/00123; A61F 2013/00604; A61F 2013/00765; A41B 11/00; A41B 11/002; A41B 11/001; A41B 11/02

See application file for complete search history.

(56) References Cited

U.S. PATENT DOCUMENTS

| | | | |
|---|---|---|---|
| 3,856,008 | A | 12/1974 | Fowler et al. |
| D234,271 | S | 2/1975 | Moore |
| 4,215,687 | A | 8/1980 | Shaw |
| 4,367,733 | A | 1/1983 | Stromgren |
| D269,816 | S | 7/1983 | Meier et al. |
| 4,476,857 | A | 10/1984 | Levine |
| 5,108,455 | A | 4/1992 | Telikicherla |
| 5,254,122 | A | 10/1993 | Shaw |
| D353,005 | S | 11/1994 | Glidden |
| D382,344 | S | 8/1997 | Swedberg et al. |
| 5,904,145 | A | 5/1999 | Reid |
| 5,906,206 | A | 5/1999 | Shaw et al. |
| 6,152,893 | A | 11/2000 | Pigg et al. |
| 6,196,231 | B1 | 3/2001 | Reid |
| 6,254,554 | B1 | 7/2001 | Turtzo |
| 6,338,723 | B1 | 1/2002 | Carpenter et al. |
| 6,516,804 | B1 | 2/2003 | Hoffman |
| 7,329,232 | B2 | 2/2008 | Lipshaw et al. |
| 8,801,645 | B2 | 8/2014 | Lipshaw et al. |
| D717,453 | S | 11/2014 | Mahtani |
| D728,804 | S | 5/2015 | Hansen |
| 9,364,701 | B2 | 6/2016 | Bartsch |
| 9,642,559 | B2* | 5/2017 | Falconio-West ........ A61F 13/08 |
| 9,642,766 | B2 | 5/2017 | Lipshaw et al. |
| D800,325 | S | 10/2017 | Cox |
| D848,625 | S | 5/2019 | Chase et al. |
| D850,632 | S | 6/2019 | Chiang et al. |
| D872,286 | S | 1/2020 | Hoffman et al. |
| 2002/0062096 | A1 | 5/2002 | Bennett |
| 2005/0113729 | A1 | 5/2005 | Scott et al. |
| 2005/0148917 | A1 | 7/2005 | Nathanson |
| 2005/0192524 | A1* | 9/2005 | Lipshaw ............... A61F 13/085 |
| | | | 602/62 |
| 2006/0201032 | A1 | 9/2006 | Ramsey |
| 2007/0179421 | A1 | 8/2007 | Farrow |
| 2010/0269240 | A1 | 10/2010 | Weir et al. |
| 2010/0312160 | A1 | 12/2010 | Creighton et al. |
| 2011/0125183 | A1 | 5/2011 | Lipshaw et al. |
| 2011/0185508 | A1 | 8/2011 | Hsu et al. |
| 2011/0257575 | A1 | 10/2011 | Farrow et al. |
| 2012/0179084 | A1 | 7/2012 | Lipshaw et al. |
| 2012/0277073 | A1 | 11/2012 | Bartsch |
| 2013/0283500 | A1 | 10/2013 | Lipshaw et al. |
| 2013/0319128 | A1 | 12/2013 | Richardson et al. |
| 2015/0025424 | A1 | 1/2015 | Richardson et al. |
| 2016/0000612 | A1 | 1/2016 | Cox |
| 2016/0030251 | A1* | 2/2016 | Schuren ............... A61F 5/0109 |
| | | | 602/75 |
| 2016/0030267 | A1 | 2/2016 | Lipshaw et al. |
| 2016/0100988 | A1 | 4/2016 | Vee et al. |
| 2016/0166458 | A9 | 6/2016 | Lipshaw et al. |
| 2017/0258672 | A1 | 9/2017 | Wennen et al. |
| 2018/0243143 | A1 | 8/2018 | Karadsheh |
| 2019/0133229 | A1 | 5/2019 | Hoffman et al. |
| 2019/0209387 | A1 | 7/2019 | Ganzoni |
| 2019/0216653 | A1 | 7/2019 | Ganzoni |

FOREIGN PATENT DOCUMENTS

| | | |
|---|---|---|
| AU | 2017329458 A1 | 2/2019 |
| AU | 2018223706 A1 | 8/2019 |
| BR | 112019002388 A2 | 6/2019 |
| BR | 112019002399 A2 | 6/2019 |
| CA | 2 722 146 A1 | 10/2009 |
| CA | 3 037 413 A1 | 3/2018 |
| CA | 3 037 417 A1 | 3/2018 |
| CA | 3 054 339 A1 | 8/2018 |
| CH | 712 938 A1 | 3/2018 |
| CH | 712 939 A1 | 3/2018 |
| EP | 1 052 319 A1 | 11/2000 |
| EP | 1 959 880 A1 | 8/2008 |
| EP | 3 512 478 A1 | 7/2019 |
| EP | 3 512 479 A1 | 7/2019 |
| EP | 3 565 515 A1 | 11/2019 |
| FR | 2 961 389 A1 | 12/2011 |
| MX | 2019001588 A | 9/2019 |
| MX | 2019001642 A | 9/2019 |
| MX | 2019009113 A | 9/2019 |
| WO | 95/16416 A1 | 6/1995 |
| WO | 99/30607 A2 | 6/1999 |
| WO | 00/15139 A2 | 3/2000 |
| WO | 01/89410 A2 | 11/2001 |
| WO | 2005/052235 A1 | 6/2005 |
| WO | 2013/085445 A1 | 6/2013 |
| WO | 2013/138394 A1 | 9/2013 |
| WO | 2014/116497 A1 | 7/2014 |
| WO | 2014/160572 A1 | 10/2014 |
| WO | 2015/188158 A2 | 12/2015 |
| WO | 2016/048827 A1 | 3/2016 |
| WO | 2016/105213 A1 | 6/2016 |
| WO | 2018/054681 A1 | 3/2018 |
| WO | 2018/054682 A1 | 3/2018 |
| WO | 2018/153611 A1 | 8/2018 |
| WO | 2019/091811 A1 | 5/2019 |

OTHER PUBLICATIONS

CircAid Arm Reduction Kit by Medi; http://mediusa.com/portfolio-item/circaid-reduction-kit/; May 20, 2016.
Solaris ReadyWrap arm sleeve by Lohmann & Rauscher; http://www.lymphedemaproducts.com/products/readywrap-arm.html; May 4, 2017.
Solaris TributeWrap Wrist to Axilla; https://www.lohmann-rauscher.com/us-en/products/solaris-collection-by-lr/tributewrap/; date unknown, at least prior to applicant's filing date of Feb. 1, 2018.
FarrowWrap Lite OTS Armpiece by Jobst; http://www.jobst-usa.com/product/jobst-farrow-ots-armsleeve/; Jul. 14, 2017.
FarrowWrap Lite Trim-To-Fit Armpiece by Jobst; http://www.jobst-usa.com/product/jobst-farrowwrap-lite-armpiece/; Jul. 14, 2017.
FarrowWrap Classic Custom Armpiece by Jobst; http://www.jobst-usa.com/product/jobst-farrowwrap-classic-armpiece/; Jul. 18, 2018.
Juzo Arm Compression Wrap; http://www.juzousa.com/Products/Product-Detail?ID= 70; date unknown, at least prior to applicant's filing date of Feb. 1, 2018.
MedAssist ArmAssist by Sigvaris; http://www.lymphedemaproducts.com/products/medassist-armassist.html; at least as of Oct. 17, 2017.
MedaFit Arm by Sigvaris; https://www.sigvaris.com/usa/en-us/product/medafit; at least as of Jun. 10, 2017.
CompreSleeve Arm by Sigvaris; https://www.sigvaris.com/usa/en-us/product/compresleeve; at least as of Jun. 10, 2017.
Notice of Allowance received for U.S. Appl. No. 29/635,709 dated Sep. 5, 2019, 18 pages.
International Search Report for International Application No. PCT/EP2018/051917 dated Mar. 12, 2018.
Non-Final Office Action received for U.S. Appl. No. 15/443,308 dated May 31, 2019, 28 pages.

(56) References Cited

OTHER PUBLICATIONS

Non-Final Office Action received for U.S. Appl. No. 15/443,308 dated Nov. 18, 2019, 17 pages.
Non-Final Office Action received for U.S. Appl. No. 15/808,092 dated Jan. 10, 2020, 32 pages.
International Search Report and Written Opinion received for PCT Application Serial No. PCT/US2019/045792 dated Oct. 28, 2019, 8 pages.
International Preliminary Report on Patentability received for PCT Application Serial No. PCT/EP2018/051917 dated Jun. 5, 2019, 10 pages.
International Search Report and Written Opinion received for PCT Application Serial No. PCT/EP2018/079569 dated Feb. 4, 2019, 8 pages.
International Search Report and Written Opinion issued in corresponding International Application No. PCT/EP2017/072213 dated Nov. 10, 2017.
International Preliminary Report on Patentability received for PCT Application Serial No. PCT/EP2017/072213 dated Apr. 4, 2019, 8 pages.
International Search Report and Written Opinion issued in corresponding International Application PCT/EP2017/072211 dated Feb. 1, 2018.
International Preliminary Report on Patentability received for PCT Application Serial No. PCT/EP2017/072211 dated Apr. 4, 2019, 16 pages.

\* cited by examiner

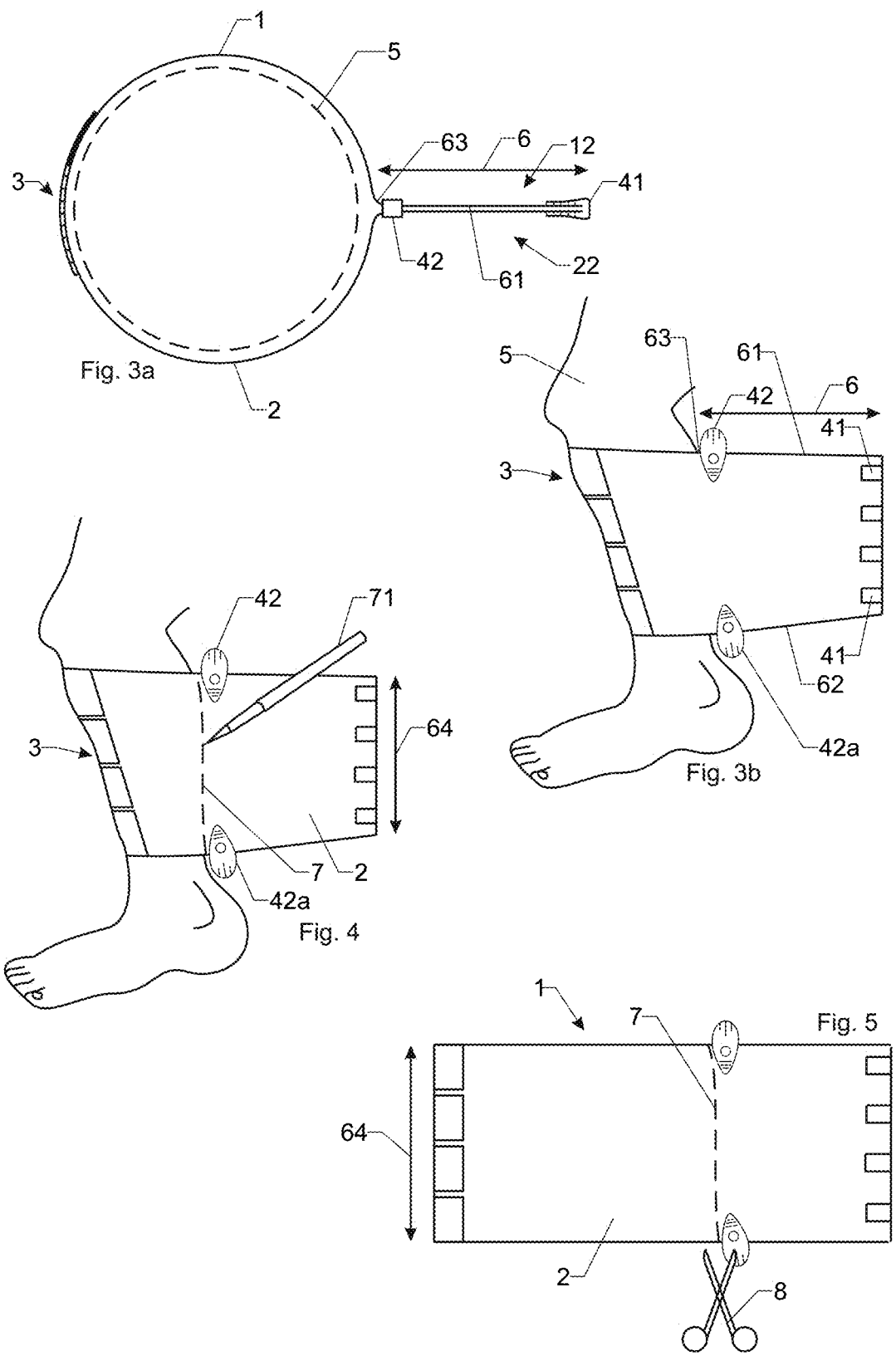

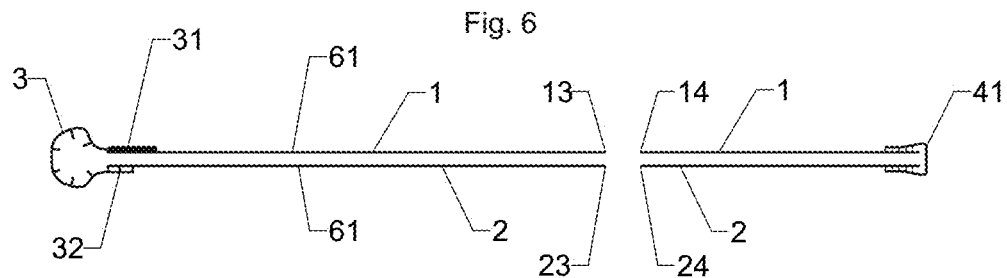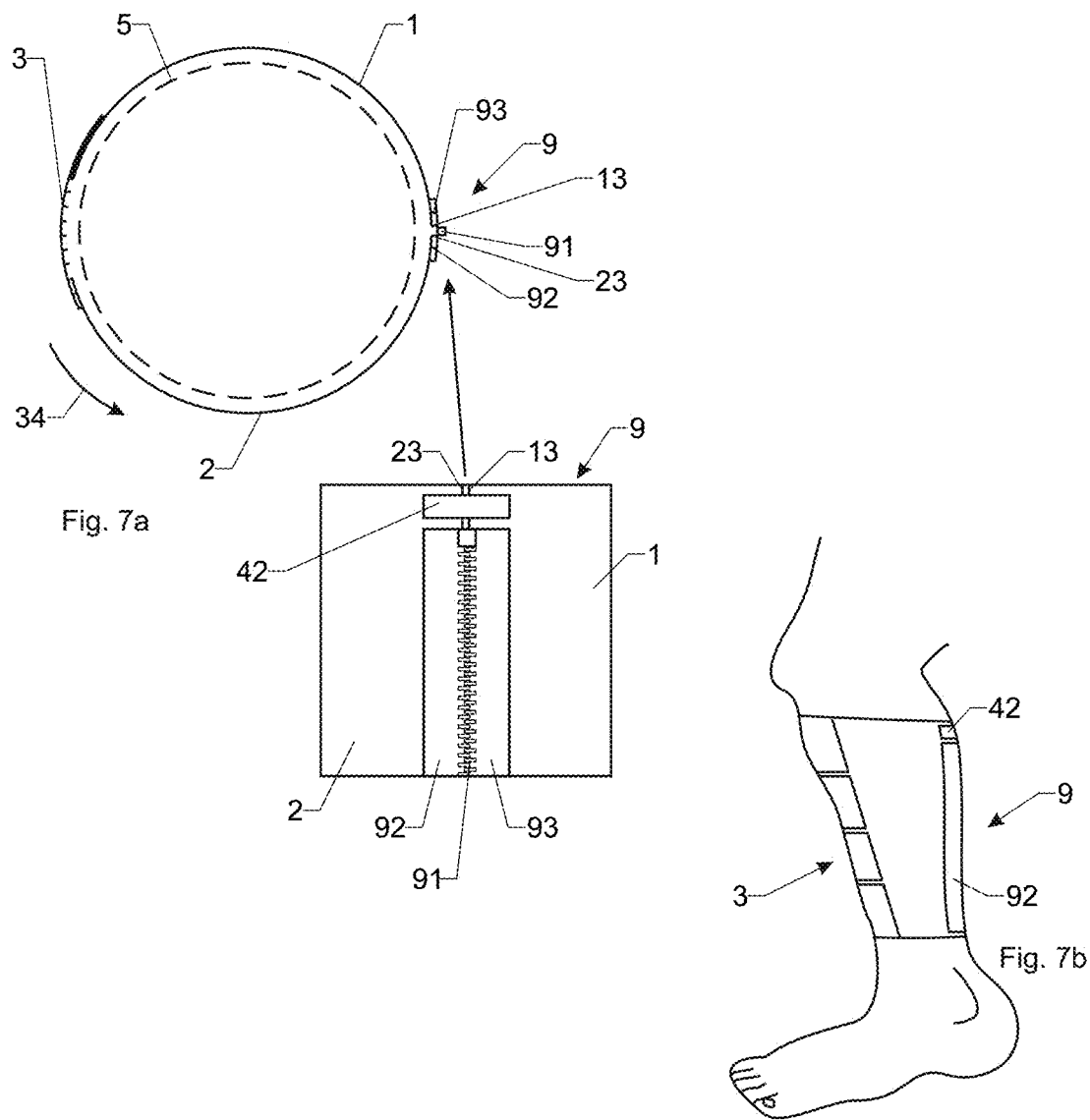

METHOD FOR TAILORING A COMPRESSION GARMENT

CROSS-REFERENCE TO RELATED APPLICATIONS

The present application claims the benefit of U.S. patent application Ser. No. 15/443,308, filed Feb. 27, 2017 and U.S. patent application Ser. No. 15/808,092, filed Nov. 9, 2017.

INCORPORATION BY REFERENCE

The disclosures of U.S. patent application Ser. No. 15/443,308, filed Feb. 27, 2017 and U.S. patent application Ser. No. 15/808,092, filed Nov. 9, 2017 are hereby incorporated by reference herein for all purposes as if presented in their entirety.

TECHNICAL FIELD

This invention relates to a method for tailoring a compression garment. The compression garment comprises a first sheet and a second sheet, each having a first lateral end and a second lateral end. Furthermore, the compression garment comprises at least one strap for holding together the first lateral end of the first sheet and the first lateral end of the second sheet, wherein said at least one strap is tightenable to establish a compression level to a human limb or body part by the compression garment. The invention further relates to a compression garment kit.

BACKGROUND ART

Edema may arise from a variety of illnesses and conditions, including venous valvular insufficiency, postphlebotic syndrome, and lymphedema. Compression methods control edema by reducing interstitial fluid.

Due to considerable variation in limb shapes and sizes, custom garments may typically be required. To facilitate the manufacture of these garments, various partially fabricated kits are available for a therapist or fitter to customize and fit a patient. Typical compression garment kits require measuring the patient to indicate cutting locations on the compression garment, in a manner that takes time and provides limited accuracy. The position of the measurement on the patient may not exactly align with the location marked on the garment, and typically only two or three measurements are transferred to the garment.

Compression garments supplied in kit form known in the art either do not provide a contoured shape to precisely fit the body part or limb, or the process for assembling the contoured shape is very tedious.

DISCLOSURE OF THE INVENTION

It is an object of the invention to provide a method for easily and quickly tailoring a compression garment to a patient.

This object is met by a method for tailoring a compression garment, said compression garment comprising
a first sheet and a second sheet, each having a first lateral end and a second lateral end,
at least one strap for holding together the first lateral end of the first sheet and the first lateral end of the second sheet, wherein said at least one strap is tightenable to establish a compression level to a human limb or body part by the compression garment,
the method including:
a first step of adjusting the at least one strap to a first position, preferably to be in position providing the largest extension of the at least one strap;
a second step of draping the compression garment around the limb or the body part;
a third step of holding the second lateral end of the first sheet and the second lateral end of the second sheet together to pull the first sheet, the second sheet and the at least one strap into contact with said limb or body part;
a fourth step of marking a cutting line on one or both sheets;
a fifth step of cutting the first and the second sheet along the cutting line;
a sixth step of splicing together both cut ends with at least one splicing element.

After having tailored the compression garment, the patient can tighten the straps in order to establish a compression to the human limb or body part.

The first step of adjusting the at least one strap can be performed by the patient or an auxiliary person. Alternatively, the first step can be performed by the manufacturer such that the straps are already correctly adjusted when the patient buys the product.

The third step can be performed by the patient or the auxiliary person by holding the first sheet and the second sheet together by hand or by a fixation element, for example. The term "second lateral end" is broadly understood. The "second lateral end" comprises all positions between the edges of the sheets and the position where the sheets start surrounding the human limb or body part. This understanding will be further explained by the description of the drawings.

The disclosed method enables the patient or an auxiliary person to easily and quickly tailor the compression garment to the individual shape and size of the patient's body part or limb. A method for custom fitting a compression garment is disclosed whereby no measurements of the patient are required to tailor a garment that is easy to assemble and fits the contour of a patient's limb or body part. Furthermore, the compression garment is appropriate for use where reduction in edema is anticipated, as it can easily be trimmed to fit a smaller body size after the edema has been reduced by the disclosed method.

The at least one strap of the compression garment provided to securing the garment in the compression state may be of the hook and loop type, or known as VELCRO® fasteners, or may comprise or include other known fastening means.

By a preferred embodiment of the method, the second lateral end of the first sheet and the second lateral end of the second sheet are held together, in particular by at least one temporary releasable fixation element, such that the lateral edges of the first sheet and of the second sheet are aligned.

If the lateral edges are aligned, the patient or the auxiliary person only needs to mark one sheet of the garment and can cut both sheets at the same time. If the edges are not aligned, one would have to mark both sheets of the garment when tailoring, and cut the two sheets independently. Furthermore, if the edges are not aligned, the first sheet and the second sheet might not have the same size and the straps might not be centered on the compression garment.

By a further preferred embodiment of the method, the second lateral end of the first sheet and the second lateral end of the second sheet are held together by arranging at least one fixation element at a top end and/or at a bottom end at the most inner meeting point of the second lateral end of the first sheet and the second sheet, and/or by arranging at least one fixation element at the lateral edges of the second lateral ends of the first sheet and the second sheet.

It is preferred that the second lateral end of the first sheet and the second lateral end of the second sheet are held together by arranging at least one fixation element directly at said limb or body part or with a small distance from said limb or said body part, preferably with a distance of at most 3 cm or at most 1 cm or at most 0.5 cm, on said lateral ends opposite to the straps. "Directly" means that the fixation element is arranged as close to the limb or the body part as possible with the normal strength of a human.

Advantageously, the splicing element comprises a slide fastener, in particular a zip fastener.

Furthermore, at the sixth step both cut ends might additionally be spliced together by the fixation element.

The exact length of the cut ends will vary, as the compression garment can be cut down in length and the cut ends are curved in shape. Since it is not desired to cut the splicing element, in particular the zip fastener, it is designed to be shorter in length than the cut ends. At least one fixation element, which has already been used for holding the sheets together while marking and cutting the sheets might be placed adjacent to the splicing element as an additional splicing element.

By a preferred embodiment, the splicing element is attached on the first sheet and on the second sheet by hook-and-loop fasteners, known as VELCRO®.

A strip of a hook surface might be sewn to each side of the zip fastener, and the strips are attached to the hook receptive surface of the garment.

Advantageously, the cutting line is marked on the garment
  directly at said limb or body part opposite to the straps, or
  with a small distance from the limb or the body part, preferably with a distance of at most 3 cm or at most 1 cm or at most 0.5 cm opposite to the straps, or
  where the first sheet and the second sheet meet opposite to the straps at the position closest to the limb or the body part.

Furthermore, a cumulated length of the first sheet and the second sheet and the at least one strap might be longer than a circumference of said limb or body before tailoring the compression garment.

By a preferred embodiment the first sheet and the second sheet extend to the full longitudinal length of the compression garment wherein the longitudinal length of the sheets is perpendicular to the lateral length of the sheets.

By a further preferred embodiment, the method comprises a further step before the first step, wherein the compression garment is pre-cut to get the size of the compression garment closer to the size of the limb before precisely tailoring the compression garment.

Furthermore, the fixation element might be a spring loaded clip.

It is another object of the invention to provide a compression garment kit that allows an easy and quick tailoring of the compression garment.

This object is met by a compression garment kit which comprises a compression garment with
  a first sheet and a second sheet, each having a first lateral end and a second lateral end,
  at least one strap for holding together the first lateral end of the first sheet and the first lateral end of the second sheet, wherein said at least one strap is tightenable to establish a compression level to a human limb or body part by the compression garment,
  a splicing element for holding together the second lateral end of the first sheet and the second lateral end of the second sheet.

The compression garment comprises an additional fixation element for temporarily holding together the first sheet and the second sheet.

Advantageously, the first sheet and the second sheet extend to the full longitudinal length of the compression garment.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 3a shows a top view and FIG. 3b a side view of a compression garment, wherein the first sheet and the second sheet are held together by several fixation elements;

FIG. 4 shows a side view of a compression garment illustrating the fourth step of marking a cutting line on one of the two sheets;

FIG. 5 shows a side view of a compression garment illustrating the fifth step of cutting the first and the second sheet along the cutting line;

FIG. 6 shows a schematic top view of a compression garment wherein the first sheet and the second sheet are cut open in two pieces;

FIGS. 7a and 7b show a compression garment wherein both cut ends of the first sheet and the second sheet are spliced together by a zip fastener.

MODES FOR CARRYING OUT THE INVENTION

An example of the method and of a compression garment kit according to the invention are now described in more detail with reference to FIGS. 1 to 7. The compression garments are made from the usual materials used for manufacturing compression garments. Such materials are known to the skilled person. In particular, the materials are different kinds of textiles which can be said as being elastic textiles or inelastic textiles within the range of forces that occur during the use of compression garments. Accordingly, the compression garments may be made of elastic materials only or may be made of inelastic materials only, or such garments may be made from a combination of elastic and inelastic materials, in particular textiles. The textiles or other materials forming together the compression garments may be connected to each other by sewing, laminating, bonding, by adhesives or glues, or by other methods or means known to the skilled person.

Figure 1:
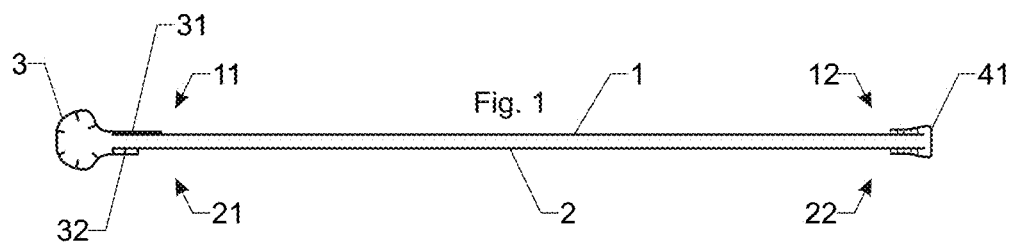
FIG. 1 shows a schematic top view of a compression garment in an initial unwrapped state before tailoring the compression garment.

In FIG. 1 an example of an unwrapped compression garment is shown in a top view. The compression garment comprises a first sheet 1 and a second sheet 2. The first sheet 1 comprises a first lateral end 11 and a second lateral end 12. The second sheet 2 comprises a first lateral end 21 and a second lateral end 22.

The first lateral ends 11 and 21 are held together by several straps 3. The straps 3 are connected to the first lateral end 11 of the first sheet 1 by a seam 31 and to the first lateral end 21 of the second sheet 2 by a hook and loop fastener 32 which are known as VELCRO®-fasteners. Alternatively, the straps could alternate with the first strap sewn to the first sheet 1, the second strap sewn to the second sheet 2, the third strap sewn to the first sheet 1, and so forth. The inner surface of the straps 3 comprises a hook layer and the outer surface of the second sheet 2 comprises a loop layer. The straps are adjustable to establish and adjust the compression during the use of the compression garment.

The second lateral ends 12 and 22 are held together by several temporary releasable fixation elements 41. The fixation elements 41 may be connected to the second lateral ends 12 and 22 by a hook and loop fastener, as shown in the figures, or any other releasable fixing means, such as a spring loaded clip.

Figure 2A:
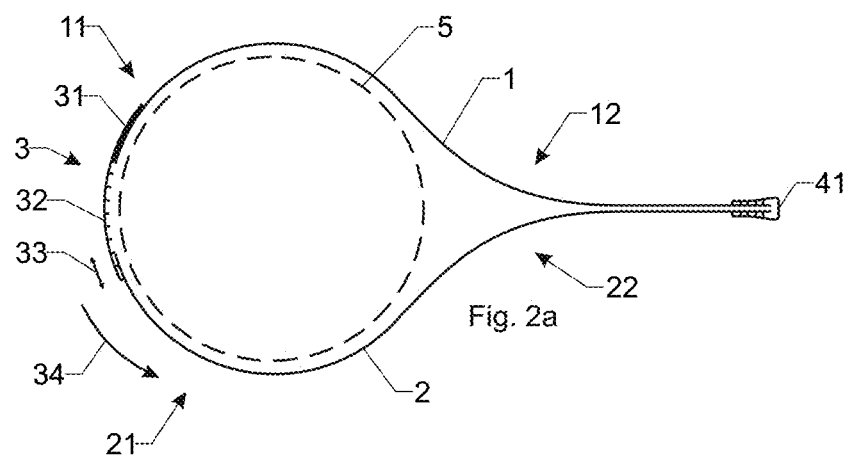
FIG. 2a shows a top view and FIG. 2b a side view of a compression garment after draping the compression garment around a leg.
Figure 2B:
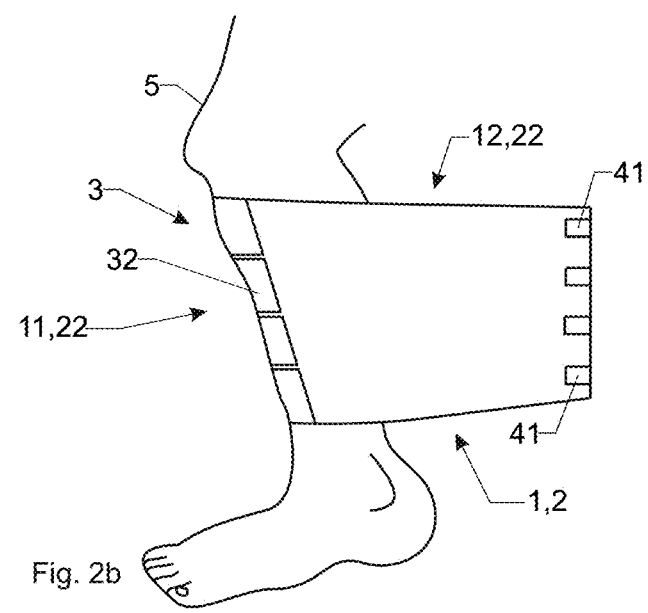

In FIGS. 2a and 2b the compression garment is draped around the leg 5 such that it is pulled into contact with the limb. The first lateral ends 11 and 21 are arranged at the front side of the leg, at the shin, or at the lateral and medial sides of the leg, and the second lateral ends 12 and 22 are arranged at the back side of the leg.

The straps 3 are in a first position providing the largest extension of the at least one strap 3. With other words, the overlap 33 between the strap 3 and the second sheet 2 is as small as possible such that the straps 3 can be tightened in the direction of the arrow 34 in order to establish compression to the leg.

In FIGS. 3a and 3b the second lateral end 12 of the first sheet 1 and the second lateral end 22 of the second sheet 2 are held together by temporary releasable fixation elements 41 and 42 while pulling the first sheet 1, the second sheet 2, and the at least one strap 3 against the leg. Preferably, enough tension will be applied to pull the first sheet 1, the second sheet 2, and the at least one strap 3 into conformity with the shape of the limb. This corresponds to the third step according to the disclosed method. The fixation elements 41 and 42 can have the same or different size and shape. In the exemplary embodiment of the figures, the fixation elements 41 are hook and loop fasteners and the fixation element 42 is a spring loaded clip.

The second lateral ends 12 and 22 of the sheets 1 and 2 are understood to comprise the whole section on the back side of the leg 5 as indicated by the arrow 6.

The fixation elements 41 are arranged at the lateral edges of the second lateral ends 12 and 22 of the first sheet 1 and the second sheet 2. The fixation element 42 is arranged at the top end 61 (the bottom end is marked with the number 62) of the sheets 1 and 2 and at the most inner meeting point 63 of the second lateral ends of the first sheet 1 and the second sheet 2. If the sheets are pulled back far enough to produce tension in the first sheet 1 and the second sheet 2, this will serve to hold the compression garment in place so that it does not fall down.

The fixation element 42 is arranged such that the second lateral end 12 of the first sheet 1 and the second lateral end 22 of the second sheet 2 are held together by the fixation element 42 directly at the leg 5 opposite to the straps 3. If desired, an additional fixation element 42a can be similarly placed at the bottom of the garment.

In FIG. 4 a cutting line 7 is marked by the marker 71. The cutting line 7 is marked on the garment and directly at the back side of the leg opposite to the straps 3. This is where the first sheet 1 and the second sheet 2 meet opposite to the straps at the position closest to the limb or the body part.

The cutting line 7 may only be marked on the second sheet 2. If the fitter does not have the capability of cutting both the first sheet 1 and the second sheet 2 simultaneously, the cutting line may be marked on the first sheet 1 and the second sheet 2.

In FIG. 5 the second sheet 2 lies on the first sheet 1 such that the first sheet 1 is not visible. The first sheet 1 and the second sheet 2 are cut with scissors 8 or a knife along the cutting line 7 over the full longitudinal length 64. The compression garment can be doffed for an easier cutting of the first sheet 1 and the second sheet 2

In FIG. 6 the compression garment is shown wherein the first sheet 1 and the second sheet 2 are cut open in two pieces and four cut ends 13, 14, 23, 24 are generated. The top or bottom edges 61 or 62 may be trimmed, if necessary, to fit the length of the limb. With other words, the longitudinal length 64 may be trimmed.

As shown in FIGS. 7a and 7b, the cut ends 13 and 23 are spliced together with a splicing element 9. The splicing element comprises a zip fastener 91. A strip with a hook surface 92 and 93 is sewn to each side of the zip fastener 91 and the zip fastener 91 is attached to the hook receptive outer surface of the first sheet 1 and the second sheet 2. To ease the assembly process, especially when the cut edges are contoured, the two sides of the zip fastener may be completely separated and each side of the zip fastener is applied individually along the cut edges 7 of the first sheet 1 and the second sheet 2.

The splicing element 9 is designed to be shorter than the compression garment because the longitudinal length 64 of the compression garment will vary, as the length of the compression garment can be cut down in length and the required splicing element length will vary if the seam is curved in shape. Therefore, both cut ends 13 and 23 are additionally spliced together by the fixation element 42 which is cut to width to fit the remaining length above the splicing element 9. A further fixation element 42 or 41 might be arranged below the splicing element.

Now, the compression garment is individually tailored and can be donned to the leg by detaching the releasable ends of straps 3 from the mating surfaces of the first sheet 1 or the second sheet 2. The straps 3 can be tightened in the direction of the arrow 34 such that the overlap between the strap 3 and the second sheet 2 is increased in order to establish compression to the leg.

If a reduction of edema occurs, the circumference of the leg decreases. The compression garment can be tailored again. For this, the straps 3 are adjusted to be in position providing the largest extension of the straps 3, the splicing element 9 is removed from the sheets 1 and 2, the lateral ends 12 and 22 are held together by arranging fixation elements 41 at the cut ends 13 and 23 and the tailoring of the compression garment is completed according to the further steps of the already disclosed method.

Figure 8A:
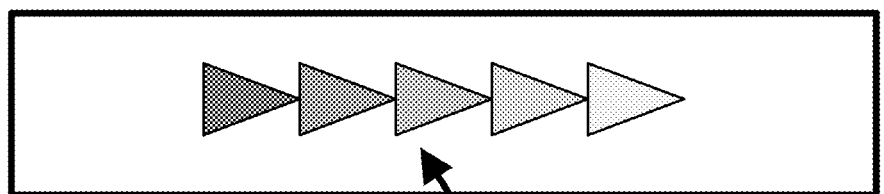
FIGS. 8A through 8C show a tension tab system that can be used with garments where the final circumference of the limb to which the garment will be applied is unknown.
Figure 8B:
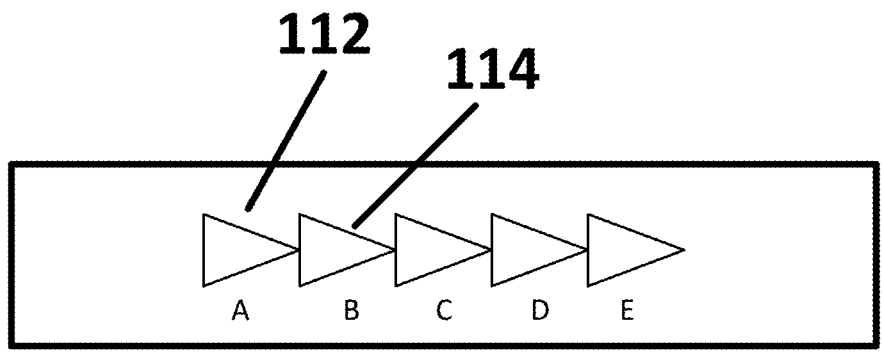
Figure 8C:
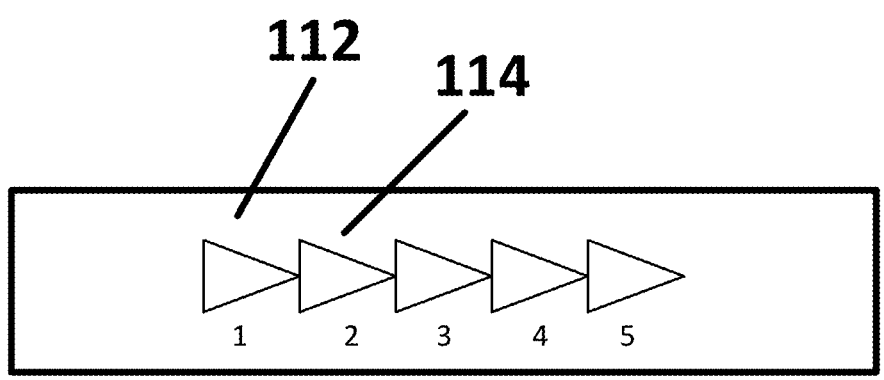

FIGS. 8A-8C show a tension tab system that can be used in conjunction with a garment where the final circumference of the limb to which the garment will be applied is unknown. One example of a garment to which the tension tabs of FIGS.

8A through 8C can be applied is where the final circumference of the limb is unknown and which is designed for application to the foot, lower leg, knee, or thigh to be fitted by a trained medical professional. In one exemplary embodiment of application of such a garment onto a patient involves a therapist first sliding the garment onto the leg with the straps open and, once the garment is in proper place, closing the straps such that they lay against the limb without tension applied to the straps. The therapist then places a clip at the top and at the bottom edge of the garment and slides the clips snugly against the back of the calf. The therapist then pinches the back panels together (keeping all centered) to create a fit around the leg, and then marks along the curve of the calf's beginning of the top of the garment and marking approximately every 5 cm to the bottom of the garment. The garment is then removed from the patient and trimmed, with the trimming separating the garment into two sections. Once trimmed to fit a patient, one half of a zipper panel is applied by hook and loop fastening to each trimmed edge of the sections of the garment. The zippers of each half of the zipper panel are then zipped together to connect the trimmed sections along the zipper panel. Optionally, a length tab can be trimmed to size and added above the zipper panel to close the back, top edges of the sections together.

In order to use the garment, the garment is arranged in place on the limb and the garment is then secured to the patient by attaching the straps onto the side of the garment opposite the zipper panel, with the straps pulled to remove slack and contact the limb, but without tension. The therapist then applies the tension tab adjacent the end of a strap. The therapist then disengages the strap from the garment and reapplies it tighter onto the garment and over a section of the tension tab. The therapist uses their professional judgment to determine how tight to pull the strap to provide the desired compression. The end of the strap is disposed over an indicator on the tension tab or generally the end of the strap falls in a range indicated by the indicator on the tension tab. The location of the end of the strap is recorded, so that the strap subsequently can be reapplied to have the end of the strap at the same position recorded by the therapist, which could occur, for example, if the strap end is moved to a different location or if the garment is removed. This procedure may be repeated with any additional straps. One exemplary discussion of the fitting procedure is detailed in commonly assigned U.S. patent application Ser. No. 15/443, 308, filed on Feb. 27, 2017, which is incorporated by reference as if repeated in entirety herein and which specifies, in part, a method of attaching a garment to a limb as shown in FIGS. 2 and 3 and detailed in the specification as:

FIG. 2 now shows the first step according to the method of the invention and shows that the compression garment has been wrapped around the limb 8 and has been provisionally secured in a first position that holds said compression garment on said limb or body part without applying a compression level to said limb or body part. By wrapping the compression garment around the limb, the outside 6 of the garment, which has not been visible in FIG. 1, is now visible. The provisional securing can be preferably done by the closing elements 7 working together with the outside of the garment. But under provisional securing within the meaning of the present invention it is also understood that this wrapping position, by which essentially no compression is applied yet, may be just held for a short while by hand by the user who has grasped the closing part 5 and has wrapped the garment around his/her limb or body part without applying a force that leads to a compression yet. But performing the following step is easier for the user when the provisional securing is done by using the closing part to secure the garment in the provisional position of the first step.

FIG. 3 serves for explaining the next or second step of the invention in which a tab 10 with an adhesive or attaching mechanism is applied to the outside of the garment, the tab 10 abutting with its one edge 10' the terminal edge 3" of the closing part 5. The tab 10 may be a paper or plastic or textile tab or a tab from a combination of such materials or may be made from yet another material. It may be provided with an adhesive that holds the tab on the outside 6 of the garment body 3 when the tab is applied to the surface of the outside 6. The tab may as well include an attaching mechanism, as for example hook and loop fastener elements, which secures the tab to the outside 6 of the garment body 3. Thus, as shown in FIG. 3 the tab 10, which is a part of the garment and is adapted to the garment's properties, defines with its opposite edge 10" a safe margin for wrapping of the compression garment around the user's limb or body part. The tab may also include a marking near the edge 10", for example a line imprinted on the tab, that indicates the safe margin instead of the edge 10".

By the next step of the method, the garment will be wrapped further around the limb or body part of the user and will be definitively secured to apply the compression level that shall be established for the intended duration of use of the garment on the user's limb or body part. This is done by grasping the bandage by the user and in this case grasping the closing part 5 and wrapping it further around the limb 8 and securing the closing part 5 to the outside 6 of the garment body 3. The closing elements 7 of the closing part will attach to the outside of the garment to this end and in particular to corresponding closing elements provided on the outside 6. The tab 10 provides the user with a clear indication which is the safe margin of wrapping and thus compressing the limb 8 or body part, since the terminal edge 10" of the tab defines a limit indicator for wrapping and securing the closing part 5 around the limb. The length of the tab 10 of the compression garment is adapted to the properties of the compression garment providing the compression. If the compression garment is mainly comprised of inelastic material, the further amount of wrapping from the non-compressive starting position shown in FIG. 3 is smaller than for a compression garment which is mainly comprised of elastic material. Accordingly, the tab 10 is shorter in the first case since the safe wrapping distance translating to a safe compression level is usually shorter than for an elastic garment, which uses a longer wrapping distance for applying compression to the limb or body part. Instead of using the terminal edge 10" as the safe level of compression indicator, a marking on the tab may be used as mentioned before.

Garments that are designed and cut at specific sizes by a manufacturer can be provided with indicators to allow a pre-sized garment to be consistently applied to a limb at a certain tension. However, if a garment has to be trimmed to size in the field, the range of circumferences a trimmed-to-fit garment will fit is typically large and an indication means cannot be easily provided to allow for consistent application of the garment onto a limb at a certain tension. For example, after a therapist has sized and trimmed a garment to a particular user, the user will need an indicator to be able to remove and then reapply the garment at the tension level recommended by the therapist.

One exemplary system that can provide an indication of a recommended tension for a user to stretch/secure the straps at tensions recommended by a therapist is shown in FIGS. 8A to 9D.

FIGS. 8A to 8C show tension tabs 100, which can be applied to a garment under or adjacent straps 3 as shown in FIGS. 9a through 9D. Using tension tabs 100 would allow a user to remove the garment, such as during a shower or for some other reason, and the user could place the garment on the limb and stretch the straps to have the strap ends fall within a tension range recommended by the therapist. The user would know where to dispose the ends of the tension tabs via indicators on the tension tabs as placed on the garment by the therapist during initially sizing/trimming. For example, once the garment has been trimmed to size and is ready for final application to the limb, the therapist can apply tension tabs with indicators on an exterior surface thereof under or adjacent the straps. The therapist can apply tension tabs under or adjacent most if not every strap, and, when the strap has been pulled to a recommended tension, the therapist can record at which indicator the end of the strap falls at, covers, or extends to. The therapist can record the marking indication for each strap to the user to remove and reapply the garment at the recommended tension levels. The user could stretch each strap to extend the strap end to fall at, cover, or extend to the indicator or indicator range. The markings could be recorded on a card or could be electronically transmitted to the user to specify where the end of each strap should be extended.

As shown in FIGS. 8A through 8C, the indicators provided on the exterior surface can be any design necessary to convey the recommended tension and can be selected from, for example, different colors, shapes, numbers, graphics, letters, or shadings. As shown in FIGS. 8A-8C, the tension tabs 100 can be provided with indicators 110, including a first indicator 112 and a second indicator 114. In the exemplary embodiment shown in FIG. 8A, the indicators 110 are shown as colored triangles, but, as detailed above, the indicators could be filled with different patterns or could be numbered or lettered as shown in FIGS. 8B and 8C. Generally, the indicators 110 indicate a range that can be recorded to indicate how tight to apply the straps 3 over the compression garment. A user can apply the straps 3 over the tension tab 100 to dispose an end of the straps 3 to overlie a specific range, such as an orange triangle, section D, section 1, or a dotted pattern (not shown). This indicator system allows a garment to be reapplied with the straps 3 to a pressure indicated by a therapist, for example, after being sized to then reapply the straps 3 within a certain range to achieve a certain amount of compression by the compression garment. For example, if the tension tab included yellow, orange, green, blue, and purple indicators, the first strap could be extended by the therapist to the orange indicator, the second strap could be extended by the therapist to the green indicator, the third strap could be extended by the therapist to the blue indicator, the fourth strap could be extended by the therapist to the orange indicator, etc.

Figure 9A:
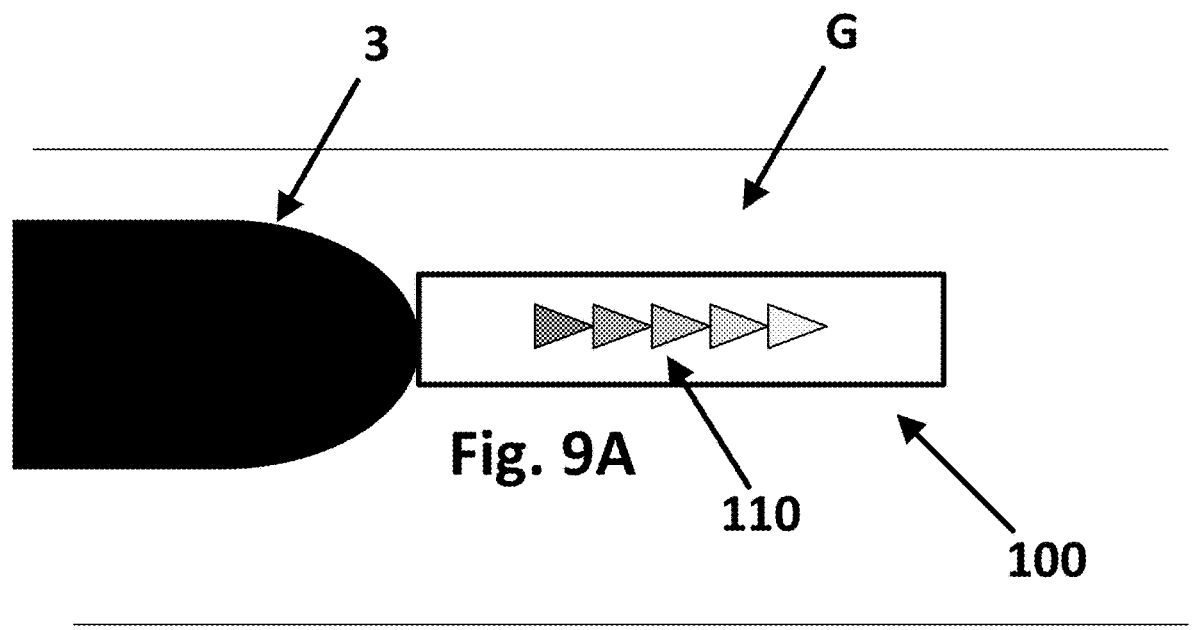
FIGS. 9A and 9B show attachment of straps over the tension tabs of FIGS. 8A through 8C.
Figure 9B:
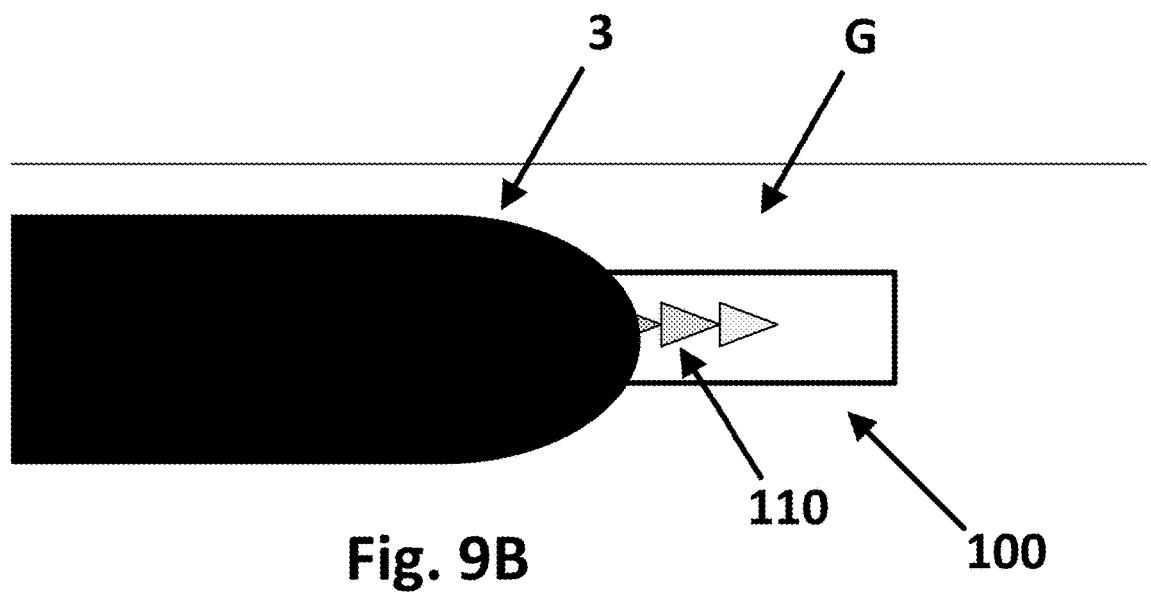
Figure 9C:
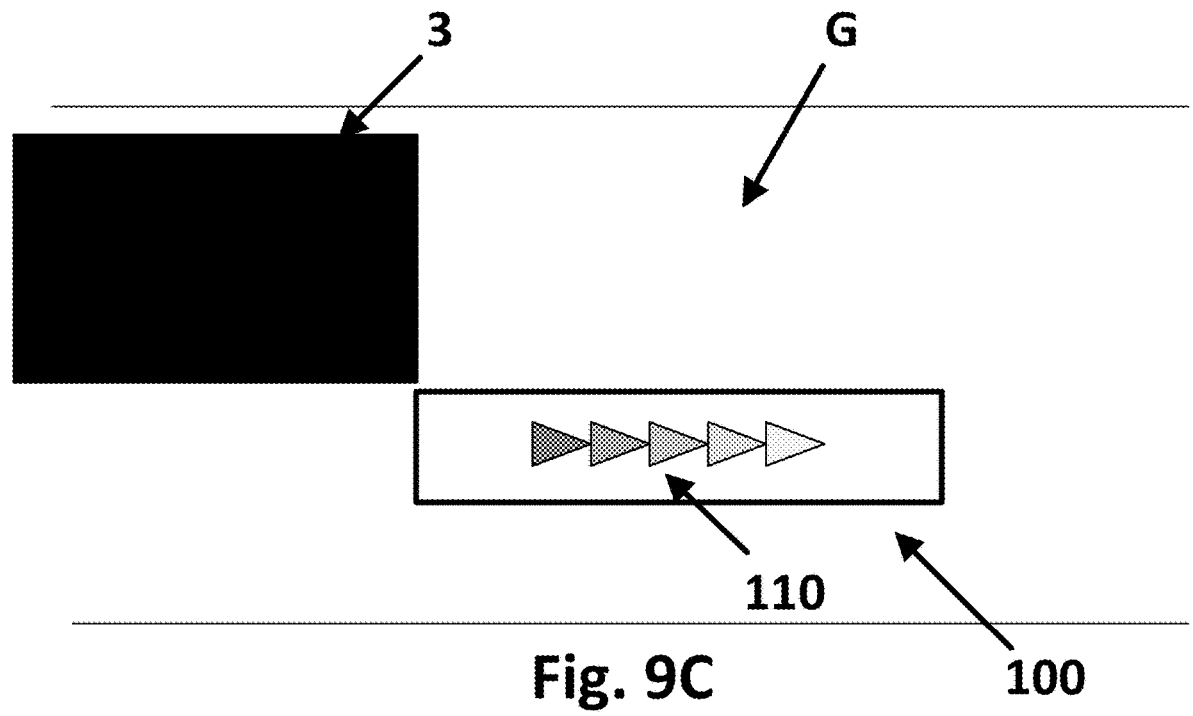
FIGS. 9C and 9D show attachment of straps adjacent the tension tabs of FIGS. 8A through 8C.
Figure 9D:
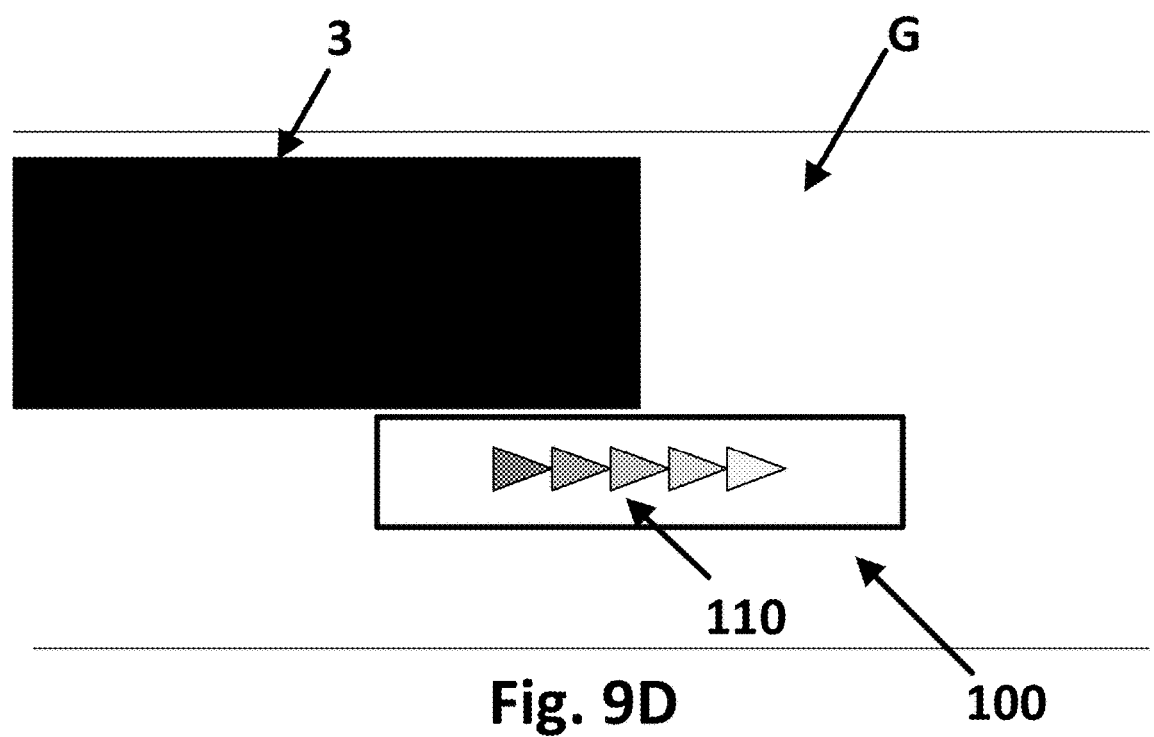

FIGS. 9A-9D show processes of applying the tension tabs of FIGS. 8A to 8C to a garment G. As shown in FIG. 9A, a strap 3 can be applied to the garment without slack but having no tension. This first location of the tension tab provides a starting point for the therapist. The tension tab can then be extended to a tension indicated by the therapist as shown in FIG. 9B. As is shown in FIG. 9B, the strap 3 ends at an indicator that can be recorded by the therapist to record the recommended tension to allow a user to extend the strap 3 to have its end at the tension indicated. FIGS. 9C and 9D show an alternative embodiment of the one shown in FIGS. 9A and 9B. In FIGS. 9C and 9D, the strap 3 is disposed adjacent the tension tab 100, as first applied to the garment in FIG. 9C and then as extended to the recommended tension in FIG. 9D. Although the strap 3 is shown below the tension tab 100 in FIGS. 9C and 9D, the tension tab 100 could be disposed above the strap 3. Even further, if desired, the therapist could trim the tension tab 100 to the desired range or some other trimming point to indicate a recommended tension.

In an alternative embodiment, a reference line could be provided on the strap and the tension tab could be initially positioned at the reference line. Then, after the strap is tightened, the position of the reference line is noted relative to the indicator on the tension tab. Although this arrangement could work with any embodiment shown above, this arrangement could be advantageous when the tension tab is positioned alongside the strap, for example in the position as shown in FIG. 9C-D. In this position, the line would be disposed near the end of the strap.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention shall not be limited to the particular embodiments disclosed, but that the invention will include all embodiments falling within the scope of the appended claims.

The invention claimed is:

1. A system for indicating tension settings of a compression garment, the system comprising:
   a first strap;
   a first tension tab releasably attachable to the compression garment; wherein the first tension tab includes at least a first indicator and a second indicator on an outer surface;
   the system operable to attach the first tension tab to the compression garment and to attach the first strap over the first tension tab; wherein the first strap covers at least part of a first portion of the first tension tab and terminates at a first strap end that exposes a second portion of the first tension tab;
   wherein a first tension tab setting indicates whether the end of the first strap terminates over the first indicator or the second indicator of the first tension tab.

2. The system of claim 1 wherein a second tension tab is attached to the compression garment; wherein the second tension tab is spaced from the first tension tab.

3. The system of claim 2 wherein a second strap is attached to the compression garment over the second tension tab; wherein a second strap covers a first portion of the second tension tab and terminates at a second strap end that exposes a second portion of the second tension tab; wherein a second tension tab setting indicates whether the end of the second strap terminates over the first indicator or the second indicator of the second tension tab.

4. The system of claim 3 wherein the first indicator and the second indicator have distinct attributes.

5. The system of claim 4 wherein the distinct attributes are different colors, shapes, numbers, graphics, letters, or shadings.

6. The system of claim 3 wherein the first indicator and the second indicator have distinct attributes.

7. The system of claim 6 wherein the different attributes are different colors.

8. The system of claim 3 wherein the first tension tab setting and the second tension tab setting are different.

9. The system of claim 3 wherein the first strap covers more of the first tension tab than the second strap covers of the second tension tab.

10. A method for indicating tension settings of a compression garment, the method comprising
   providing the compression garment having a first strap;
   attaching a first tension tab to the compression garment;
      wherein the first tension tab includes at least a first indicator and a second indicator on an outer surface;
   attaching the first strap over at least a portion of the first tension tab; wherein the first strap covers a first part of the first tension tab and terminates at a first strap end that exposes a second part of the first tension tab;
   wherein a first tension tab setting indicates whether the end of the first strap terminates over the first indicator or the second indicator of the first tension tab.

11. The method of claim 10 further comprising:
   attaching a second tension tab to the compression garment; wherein the second tension tab is spaced from the first tension tab.

12. The method of claim 11 further comprising
   attaching a second strap onto the compression garment over the second tension tab;
      wherein a second strap covers a first portion of the second tension tab and terminates at a second strap end that exposes a second portion of the second tension tab; wherein a second tension tab setting indicates whether the end of the second strap terminates over the first indicator or the second indicator of the second tension tab.

13. The method of claim 12 wherein the first indicator and the second indicator have distinct attributes.

14. The method of claim 13 wherein the distinct attributes are different colors, shapes, numbers, graphics, letters, or shadings.

15. The method of claim 12 wherein the first tension tab setting and the second tension tab setting are different.

16. The method of claim 12 wherein the first strap covers more of the first tension tab than the second strap covers of the second tension tab.

17. The method of claim 10 wherein the first indicator and the second indicator have distinct attributes.

18. The method of claim 17 wherein the different attributes are different colors.

* * * * *